United States Patent [19]

Shuttleworth et al.

[11] 4,054,599

[45] Oct. 18, 1977

[54] SULFOXIDATION PROCESS

[75] Inventors: Henry Shuttleworth; Wahid R. Ali, both of Pointe-a-Pierre, Trinidad And Tobago

[73] Assignee: Texaco Trinidad, Inc., Pointe-a-Pierre, Trinidad And Tobago

[21] Appl. No.: 608,112

[22] Filed: Aug. 27, 1975

Related U.S. Application Data

[63] Continuation-in-part of Ser. No. 326,347, Jan. 24, 1973, abandoned.

[51] Int. Cl.² ............................................. C07C 143/02
[52] U.S. Cl. ................................................ 260/513 R
[58] Field of Search .................................... 260/513 R

[56] References Cited

U.S. PATENT DOCUMENTS 3,743,673   7/1973   Downer et al. ............... 260/513 R

*Primary Examiner*—James O. Thomas, Jr.
*Assistant Examiner*—Nicky Chan
*Attorney, Agent, or Firm*—Thomas H. Whaley; Carl G. Ries; Henry W. Archer

[57] ABSTRACT

Saturated aliphatic hydrocarbons are converted to color-stable aliphatic sulfonic acids in a single step without any initiator but in the presence of a low molecular weight acyl oxide and under anhydrous conditions by the rapid removal of the products as they are being formed, followed immediately by cooling and degassing to remove sulphur dioxide, then by immediate neutralization and complete hydrolysis at the boiling point of the unstable acid precursors present in the neutralized sulphonates by boiling at constant volume at a pH of about 8-10. The alkali metal salts of the sulfonic acids prepared by this process are color and pH-stable and useful as biodegradable detergents.

7 Claims, No Drawings

SULFOXIDATION PROCESS

CROSS-REFERENCE TO CO-PENDING APPLICATION

This application is a continuation-in-part of coassigned application Ser. No. 326,347, filed Jan. 24, 1973 and now abandoned.

BACKGROUND OF THE INVENTION

This invention relates to a sulfoxidation process and more particularly to a process for converting paraffins to biodegradable alkali metal salts of sulfonic acids.

The present invention constitutes an improvement over the process disclosed and claimed in commonly assigned U.S. Pat. No. 3,743,673 issued July 3, 1973, the disclosure of which is incorporated by reference in the instant application.

The process disclosed in the above-mentioned patent has been found at times to yield products which are not color and pH stable owing mainly to ferric contamination due to plant conditions such as the use of certain iron alloys. In U.S. Pat. No. 3,743,673 no disclosure was made of an immediate separation of the heavy product phase from the unreacted paraffin charge. It has now been found that allowing the heavy product phase to remain at the reaction temperature and in the presence of sulfur dioxide as described in the patent causes irreversible changes in the product; the resulting final product's color and color stability cannot be then improved by normal working-up procedures.

U.S. Pat. No. 3,743,673 also teaches that free gases should be vented from the settler tank. This procedure causes the heavy product phase to remain in the presence of dissolved sulfur dioxide which causes adverse effects on the color of the product.

U.S. Pat. No. 3,743,673 also did not teach the hydrolysis of the separated and degassed heavy product phase over an optimum period of time and at the boiling point of the phase to completely hydrolyse the acid precursors present therein. Such hydrolysis now has been found essential for the obtaining of color stable products.

SUMMARY OF THE INVENTION

The present invention provides a one-step sulfoxidation process for making color-stable sulfonic acids from which valuable biodegradable detergents can easily be made.

Briefly stated, the process of the invention comprises (1) reacting in a reaction zone substantially straight chained paraffins of about 7 to 24 carbon atoms per molecule with oxygen and sulfur dioxide under substantially anhydrous conditions in the presence of about 1 to about 4 percent by weight of acetic anhydride or other low molecular weight acyl oxide having from 2 to 8 carbon atoms at a temperature of about 25° to 55° C. under pressures of from about 0 to about 100 psig while agitating the reactants; (2) immediately and continuously separating the heavy product phase as it forms from unreacted paraffins thereby removing acid products from the reaction zone; (3) cooling the product phase; (4) degassing the cooled product phase; (5) neutralizing the product phase to a pH of 8 to 10 by adding an alkali metal hydroxide; (6) hydrolyzing the acid precursors present in the product phase by boiling the product phase at substantially constant volume and at a pH of 8-10; (7) and removing solid contaminant materials present in the product phase to yield color stable alkali metal sulfonates.

Straight-chained, saturated hydrocarbons having up to 30 carbon atoms per molecule and higher, can be sulfoxidized provided the feedstock is present as a liquid over the desired reaction temperature rnge. n-Paraffins which are normally solid over the range 25°-55° C. may be sulfoxidized in solution in an inert solvent; e.g. halogenated hydrocarbons, or in admixture with liquid n-paraffins. Separation is preferably by centrifuging carried out at 40 X G. for 2 minutes. More severe centrifugal separation can precipitate the reactive intermediate as well as the heavy product phase and stop the reaction.

Hydrolysis of the unstable acid precursors present in the neutralized sulphonates is effected by boiling a 20% w/w aqueous sulphonates solution at constant volume for 12 hours at a pH between 8 and 10. This procedure has been found most important for the obtaining of a low colored, pH-and color-stable product. Part of the discoloration of sulphonates prepared under plant conditions is due to ferric hydroxide contamination from iron-alloy vessels, and this can best be removed by filtering the alkaline solution after hydrolysis of the unstable acid precursors in the sulphonates to remove such contaminants therefrom.

With the process of this invention, a low color-and pH-stable product which remains stable upon standing is obtained and the formation of bi-functional product and by-product sulfuric acid is minimized because the heavy product phase is removed from the reaction as soon as it is formed and because it is worked up immediately, is prevented from reacting further.

DETAILED DESCRIPTION OF THE INVENTION

The paraffin reactants used in the present process can be of a single species, e.g. n-undecane, but generally will be fed to the reaction zone in the form of a mixture comprising paraffins containing from 7 to 24 carbon atoms per molecule. It has been noted that the presence of even as little as 0.01% of aromatics or of olefins inhibit the reaction and produce a very dark colored reaction medium. Accordingly, the paraffin feed should be oleum-treated to remove all but 0.01% by weight of these materials. The feed can contain up to 2.0% by weight of branched-chain material but normally will consist essentially of straight chained material.

The reaction rate is limited by the length of the chain reaction, and is dependent on a number of interrelated factors, the most important being concentration of free radicals, the temperature and pressure of the reaction, and mass transfer. The number of free radicals required for sustained reaction varies according to the reaction conditions, the concentration of reactants and the molecular weight of the feedstock. Perhaps the most important factor is that the concentration of free radicals is directly proportional to the rate of decay of an alkyl-acetyl-sulfonyl peroxide. The decay rate equation was shown to be a first order reaction of the form:

$$\log_{10} C = 0.4343\, Kt + \log_{10} C_0$$

where $C_0$ is the initial concentration, $C$ the concentration at time $t$, and $K$ the rate constant.

The rate constant $K$ decreases with increase in the chain length of the alkyl group. Thus, as the feedstock gets heavier more peroxide intermediate is required for sustained reaction; this is achieved by increasing the acetic anhydride concentration. The optimum acetic anhydride concentration ranges from 1 to 3% weight for a feedstock which ranges in carbon content from $C_{11}$ to $C_{18}$. Increasing the concentration much above 3% has no significant effect on conversion or on product distribution over the pressure range of 0-75 psig.

It has been found that rapid separation of the heavy phase, in accordance with the present invention, signifies that reactive intermediate material (chain reaction initiator and precursor materials) present in the paraffin phase is being removed from the reaction zone. As a result, the "per content" or amount of alkylacetyl-sulfonyl peroxide falls and so does the reaction rate. This can be countered by adding extra acetic anhydride to maintain the "per" value at the "threshold" level below which the reaction rate is proportional. In practice, the recycle paraffin stream is combined with incoming fresh paraffin before being fed to the reactor. This stream is automatically supplied with a controlled and metered amount of acetic anhydride so that the optimum "per content" of the recycle paraffin phase is just exceeded. This extra acetic anhydride is about one-fifth of that initially used.

An increase in reaction pressure over the range 0-75 psig brings about an increase in reaction rate, that is where mass transfer is rate determining. This increase in reaction rate as the pressure increases becomes more pronounced the higher the molecular weight of the paraffin charge and is accompanied by an increase in conversion to di- and polysulfonic acids.

Experimental data have shown that the optimum reaction temperature is 35° C. While the decomposition of the peroxide intermediate is dependent on temperature, the reaction rate is not dependent on the peroxide as long as the peroxy content is above a certain value which varies with the molecular weight of the paraffin. The maximum peroxide content attainable decreases with an increase in temperature above 35° C. It has been shown that there is no significant change in reaction rate when increasing the temperature from 35° to 55° C; however, the percent weight polysulfonates in the product increases and the color darkens.

The mass transfer will depend upon the mixing conditions and gas dispersion. Within broad limits, neither the recycle rate nor the impeller speed has an appreciable effect on reaction rate or product composition. At any given pressure (0-75 psig) the reaction rate increases linearly with increase in the $SO_2/O_2$ ratio of the reactor gas, up to a maximum beyond which the rate decreases. However, the monosulfonic acids content of the total sulfonic acids produced decreases linearly with increase in $SO_2/O_2$ reactor gas ratio. Thus an increase in both reaction pressure and $SO_2/O_2$ reactor gas ratio leads to the formation of more polysulfonic acids. This effect is also produced by leaving the heavy product phase in the reaction zone. Quality-wise, however, these poly acids can be tolerated in a commercial detergent. The reaction rate increases with the gas rate but the sulfonic acids: sulfuric acid ratio decreases. The gas rate does not influence the rate of decay of the peroxide intermediate.

This process results in two principal by-products, sulfuric acid and polysulfonic acids. Both are wasteful in $SO_2$ but neither has an appreciable effect on the process or on the product quality.

The first of these is formed by reactions inherent in the sulfoxidation reaction mechanism, e.g. (a) $RSO_2$-$OOH + SO_2 + H_2O \rightarrow RSO_3H + H_2SO_4$. This is more prevalent in the light/water process where water is added. It is possible in the present anhydrous process because water can be formed. (b) $3RH + 4SO_2 + 2H_2 \rightarrow 2RSO_3H + RSO_2OSO_2OH$; $RSO_2O SO_2OH + H_2O \rightarrow RSO_3H + H_2SO_4$.

Though the effects of water to produce sulphuric acid are presented in the 2nd equation, no water-forming reactions are shown. Graf (ref. Ann., 1957, 578, 50) states that water is formed by the reactions

$RSO_3OH \rightarrow RSO_3. + HO.$

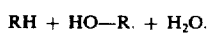

$RH + HO \rightarrow R. + H_2O.$

GENERAL WORKING PROCEDURE

Fresh normal paraffins and acetic anhydride and recycle normal paraffins are charged continuously to the top of a stirred tank reactor. A mixture of sulfur dioxide and oxygen enter through the bottom of the reactor. The reactor is equipped with baffles and a high speed agitator to ensure good liquid/gas mixing. The reactor contents are maintained at 35° C. by continuous circulation through an outside loop fitted with a heat exchanger. This effectively removes reaction heat and also assists the mixing of reactor ingredients. A vent stream leaving the top of the reactor is routed to a vapor liquid separator for removal and return to the reactor of entrained liquid. The gases remaining are passed to a gas holder for eventual recycle back to the reactor.

The product sidestream is continuously withdrawn from the reactor loop and passed to a settler for the separation of crude acid and unreacted paraffin phases. The paraffins are taken from the top of the settler to a surge tank for intermediate storage prior to recycling back to the reactor. Any free gases carried into the settler are released through a vent line leading to the gas holder. The separated heavy crude acid pase is then cooled rapidly to 10° C. and degassed free of sulphur dioxide as quickly as possible either by using an air, oxygen or an inert gas and/or using a vacuum. $SO_2$ has a deleterious effect on product color and must be removed as completely as possible. The heavy crude degassed acid phase is routed to a mixing pump for part neutralization to pH = 7-10 with 30% NaOH at 10° C. Unreacted paraffin is separated off and hydrolysis of the unstable acid precursors is then carried out by boiling the neutralized aqueous sulphonates for at least 12 hours at atmospheric pressure. During this period, the volume of solution is maintained constant at about 20% of sulfonates, basis weight of solution, and the pH must be kept between 8-10 by additions of an alkali metal hydroxide. The hydrolysis period can be shortened to about 2 hours by using higher temperatures.

The following example is given to illustrate the present invention.

EXAMPLE 1

In a typical sulfoxidation run a mixture of $nC_{14-18}$ paraffins containing 3% w/w acetic anhydride was sulfoxidized by gassing with 20 l./hr. sulfur dioxide and 10 l./hr. oxygen in a stirred tank reactor. The 1 liter of charge was recycled at 2 l./hr. through a 500 ml. separator and heavy product phase was allowed to separate out.

By incorporating an in-line centrifuge operating at 40 × gravity in place of a separator, the heavy product phase is separated from the paraffin phase as quickly as it is formed. The separated heavy phase is quickly cooled to just above 0° C. and preferably to approximately 10° C. It is degassed free of sulphur dioxide using an inert gas or vacuum as quickly as possible. The degassed cooled phase is then neutralized to a pH of 8-10 at 10° C. Hydrolysis of the neutralized heavy product phase which is an important stage in the attainment of color-stable sulphonates, is achieved by boiling a 20%-wt. aqueous sulphonate solution for 10 to 14 hours and preferably for 12 hours at substantially constant volume and at a pH of 8-10. The resulting product consists of sodium sulphonates having improved color and stability.

TABLE I

| Time Intervals (hrs.) | Drying Sequence | Centrifuged Klett No. | pH | Recycle Klett No. | pH |
|---|---|---|---|---|---|
| | Initial | 2 | 10.4 | 15 | 11.3 |
| 8 | 1st Drying | 7 | 10.0 | 27 | 10.0 |
| 16 | 2nd Drying | 9 | 10.0 | 42 | 10.0 |
| 24 | 3rd Drying | 9 | 9.9 | 45 | 9.4 |
| 32 | 4th Drying | 10 | 10.0 | 48 | 9.6 |

The color stability test used in this work is the overnight drying down of 50 mls. of a 5% w/w aqueous solution of the sulphonate above obtained on a water bath and the reconstitution to the original state in water. This procedure was repeated and colour (Klett No. at 420 mμ) and the pH were determined as shown in Table I.

The color evaluation of the product is based on the method described in I. Biological Chem. 130, 149-66 (1939) and uses a Klett-Summerson glass cell photoelectric colorimeter. The scale of reference in measurements made with this instrument of Klett Number assigns a high number to a dark product. The Klett Number of a commercial detergent is 20.

Referring to Table I above, it is evident that the centrifuged product in each case was lighter and more color-stable than when the product phase was recycled back to the reactor. It should also be noted that in common with commercial detergents, the Klett Number of the centrifuged sample did not increase by more than two with each successive drying. This should be contrasted with the considerable darkening noted with the recycled material which goes from a Klett Number 15 to Klett Number 48 after four dryings.

Degassing the heavy product phase free from sulphur dioxide must be achieved at as low a temperature as can be carried out without having to deal with a solid phase. This must be done as quickly as possible; in fact the whole operation of (1) isolating the heavy product phase as soon as formed by centrifuging (2) cooling the heavy product phase to just above the setting point and (3) at the same time degassing the heavy product phase free of sulphur dioxide, is one of urgency. At this stage the degassed heavy product phase is diluted with water or neutralised, and this too must be done reasonably quickly. It is necessary to understand that heavy product phase formed during the sulphoxidation is reacting-/decomposing all the time. A comparison of stabilities may be presented as follows:

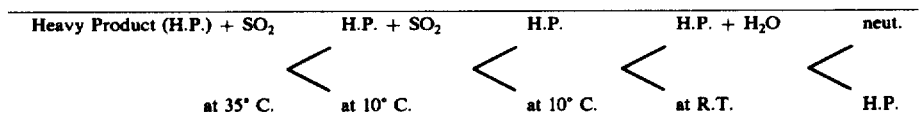

| Heavy Product (H.P.) + $SO_2$ at 35° C. | < | H.P. + $SO_2$ at 10° C. | < | H.P. at 10° C. | < | H.P. + $H_2O$ at R.T. | < | neut. H.P. |

The above comparison is based on tests which showed that when any one of the above three steps is omitted the product is not color stable.

We claim:

1. In a sulfonation process wherein ferric hydroxide contamination due to iron alloys reactors is avoided comprising reacting, in a reaction zone, substantially straight chain saturated liquid hydrocarbons with oxygen and a sulfur dioxide under substantially anhydrous conditions in the presence of about 1 to about 4 percent by weight of a low molecular weight aliphatic acyl oxide having from 4 to about 8 carbon atoms at temperatures of about 25° to about 55° C. under a pressure ranging from about 0 to 100 psig, the improvement which comprises continuously removing the resulting heavy product phase from the reactants to separate said phase as soon as it forms from unreacted hydrocarbons; cooling said phase to between above 0° C and 10° C and immediately degassing said phase free of sulfur dioxide; neutralizing the acid in said separated phase at a pH of 8-10; hydrolyzing unstable acid precursors present in said phase by boiling said phase at substantially constant volume at said pH, for about 10 to about 14 hours, filtering solid contaminants from said phase; and recovering color-stable sulphonates from the hydrolyzed phase.

2. The process of claim 1, wherein said paraffins are initially treated with oleum to remove all but about 0.01 per cent by weight of aromatic or olefinic materials.

3. Process according to claim 1, wherein the inlet ratio (vol.) of sulfur dioxide to $O_2$ ranges from 2 at 0 psig to 3 at 75 psig.

4. Process according to claim 1, wherein the pressure ranges from 0 to 25 psig.

5. Process according to claim 1, wherein said acyl oxide is acetic anhydride.

6. Process according to claim 1, wherein said product phase is removed by centrifuging carried out at about 40 X gravity.

7. The process according to claim 1, comprising providing an excess of said acyl oxide to prevent a decrease in the reaction rate of formation of said sulfonates.

* * * * *